United States Patent [19]

Müller-Schiedmayer et al.

[11] 4,240,980
[45] Dec. 23, 1980

[54] PROCESS FOR THE MANUFACTURE OF N,N,N',N'-TETRAACETYLETHYLENEDIAMINE

[75] Inventors: Günther Müller-Schiedmayer; Rudolf Aigner, both of Burgkirchen, Fed. Rep. of Germany

[73] Assignee: Hoechst Aktiengesellschaft, Fed. Rep. of Germany

[21] Appl. No.: 29,258

[22] Filed: Apr. 11, 1979

[30] Foreign Application Priority Data

Apr. 14, 1978 [DE] Fed. Rep. of Germany ....... 2816174
Feb. 21, 1979 [DE] Fed. Rep. of Germany ....... 2906606

[51] Int. Cl.$^3$ .......................................... C07C 102/00
[52] U.S. Cl. .................................................... 564/153
[58] Field of Search .................................... 260/561 R

[56] References Cited

U.S. PATENT DOCUMENTS

| | | | |
|---|---|---|---|
| 3,223,732 | 12/1965 | Viveen et al. | 260/561 R |
| 3,539,629 | 11/1970 | MacKellar et al. | 260/561 R |
| 3,824,286 | 6/1974 | Grimmelikhuysen | 260/561 R |
| 3,824,287 | 6/1974 | Mattias et al. | 260/561 R |
| 3,886,212 | 5/1975 | Kunstle et al. | 260/561 R |

FOREIGN PATENT DOCUMENTS 1373308  12/1974  United Kingdom .

OTHER PUBLICATIONS

The Merck Index, 7th ed. 1960, p. 210.

*Primary Examiner*—Arthur P. Demers
*Attorney, Agent, or Firm*—Connolly and Hutz

[57] ABSTRACT

The invention provides an improved process for the manufacture of N,N,N',N'-tetraacetylethylenediamine by acetylation of N,N'-diacetylethylenediamine with acetic anhydride, by using these two starting components in a weight ratio of from 1:1 to 1:10, stopping the acetylation before attaining the reaction equilibrium between N,N'-diacetylethylenediamine and N,N,N',N'-tetraacetylethylenediamine, preferably after having attained a conversion rate of from 20 to 70 mol % of tetraacetylethylenediamine, relative to diacetylethylenediamine, purifying the reaction mixture in order to remove the dyeing impurities, and recycling to the acetylation the purified, incompletely reacted components. Purification may be carried out by vacuum distillation or by means of an adsorbent, for example bleaching earth or active charcoal. Optionally, from 0.01 to 0.3 part by weight of ketene per part by weight of diacetylethylenediamine are added to the starting components. The process may be carried out batchwise or continuously, and it gives a practically colorless product with high yield (more than 97%).

8 Claims, No Drawings

PROCESS FOR THE MANUFACTURE OF N,N,N',N'-TETRAACETYLETHYLENEDIAMINE

N,N,N',N'-Tetraacetylethylenediamine is an important additive for detergents, where it serves as perborate activator. According to German Offenlegungsschrift No. 19 10 300, this compound can be manufactured by reaction of ethylenediamine or N,N'-diacetylethylenediamine with ketene in the presence of solvents and catalysts. However, this process requires much technological expenditure, and the catalysts as well as the solvent must be carefully separated from the tetraacetylethylenediamine produced.

Tetraacetylethylenediamine can be obtained furthermore by prolonged boiling of N,N'-diacetylethylenediamine with acetic anhydride (German Auslegeschrift No. 21 33 458 or Rec. Trav. Chim., Vol. 30, 1911, pp. 183-185). This process, however, has the disadvantage of giving relatively poor yields. Furthermore, the color of the product does not meet the requirements.

German Pat. No. 21 18 281 discloses that tetraacetylethylenediamine can be manufactured continuously by reacting diacetylethylenediamine with acetic anhydride at 120° to 170° C., distilling off simultaneously the acetic acid formed from the reaction mixture, crystallizing and separating the tetraacetylethylenediamine by cooling the reaction mixture, and recycling part of the residual dark-brown reaction mixture to the reactor. The acetic acid is removed during the reaction by fractional distillation, so that, because of poor separation of acetic acid and acetic anhydride, the content of the latter substance in the reaction mixture is gradually decreased. This process requires therefore the use of a large excess of acetic anhydride. After cooling, crystallization and separation of the tetraacetylethylenediamine formed, a dark-colored solution in acetic anhydride containing considerable amounts of incompletely reacted components remains. A further serious disadvantage of this process resides in the fact that 50 to 90 weight % only of the reaction product remaining after the separation of solid tetraacetylethylenediamine can be recycled to the reaction zone, in order not to deteriorate in advance the color of the tetraacetylethylenediamine to be formed. Despite work-up of the amount of reaction mixture discharged and recovery of excess acetic anhydride by distillation, by-products in the form of liquid, brown residues remain in such large amounts that a total yield of a maximum 86 weight % of tetraacetylethylenediamine only can be attained. Furthermore, relatively long reaction times are required, thus causing the formation of relatively large amounts of by-products.

Subject of the present invention is an improved process for the manufacture of N,N,N',N'-tetraacetylethylenediamine by acetylation of N,N'-diacetylethylenediamine with acetic anhydride at a temperature of from 120° to 170° C., which comprises (a) using N,N'-diacetylethylenediamine and acetic anhydride in a weight ratio of from 1:1 to 1:10, (b) stopping the acetylation before the reaction equilibrium between N,N'-diacetylethylenediamine and N,N-N',N'-tetraacetylethylenediamine is attained, (c) purifying the brown-colored reaction mixture after or before the separation by crystallization of N,N-N',N'-tetraacetylethylenediamine, in order to remove the dyeing impurities, and (d) recycling the purified and recovered reaction components not completely reacted to the acetylation.

The process of the invention gives a nearly quantitative yield of practically colorless N,N,N',N'-tetraacetylethylenediamine without formation of significant amounts of useless by-products.

The N,N'-diacetylethylenediamine is acetylated under normal pressure or slightly elevated pressure, for example up to about 5 bars, preferably from 1 to 2 bars, and at a temperature of from 120° to 170° C., preferably 130° to 160° C. Advantageously, the N,N'-diacetylethylenediamine is used in industrial grade purity; small amounts of water up to about 1 weight %, and acetic acid up to about 5 weight % do not cause any trouble.

The weight ratio of N,N'-diacetylethylenediamine to acetic anhydride (advantageously used in industrial grade purity, too) is from 1:1 to 1:10, preferably from 1:1 to 1:5, especially from 1:1 to 1:2.5.

According to this invention, the reaction (acetylation) of N,N'-diacetylethylenediamine with acetic anhydride is stopped before the reaction equilibrium of N,N-N',N'-tetraacetylethylenediamine and N,N'-diacetylethylenediamine is established, preferably after having attained a conversion rate of from 20 to 70 mol %, especially 40 to 60 mol %, of tetraacetylethylenediamine, relative to the molar amount of N,N'-diacetylethylenediamine. Advantageously, this interruption is ensured by dropping the temperature of the reaction mixture (product mixture) to below 120° C., preferably 20° to 110° C., especially 60° to 100° C. (optionally the feed of reactants is simultaneously stopped). The conversion degree can be determined in simple manner, for example by analysis, or by weighing out the crystallized N,N,N',N'-tetraacetylethylenediamine (determined from an aliquot amount of reaction mixture). After having recycled the reaction products not completely converted to N,N,N',N'-tetraacetylethylenediamine, the indicated conversion degree is calculated likewise on N,N'-diacetylethylenediamine, that is, the N,N-N',N'-triacetylethylenediamine contained therein, which is likewise capable of reacting further, is calculated as N,N'-diacetylethylenediamine.

The acetylation of N,N'-diacetylethylenediamine with acetic anhydride is advantageously carried out as follows: fresh N,N'-diacetylethylenediamine and the reaction components incompletely converted and recovered after the purification in accordance with the invention (that is, the purified product mixture liberated from tetraacetylethylenediamine and acetic acid) which consist substantially of a mixture of diacetyl- and triacetylethylenediamine, are reacted batchwise with acetic acid anhydride with agitation (in order to ensure homogeneous intermixing) and in the weight ratio as indicated above. This batchwise reaction is preferably carried out by refluxing in a reactor provided with agitator and reflux condenser. The conversion rates in accordance with the invention are generally attained after 0.5 to 5, preferably 1.5 to 3, hours.

It is especially advantageous to carry out the reaction continuously in several series-connected reactors arranged preferably in a cascade of two to five, especially two or three, and provided with agitator and reflux condenser. In this case, N,N'-diacetylethylenediamine, the product mixture recovered after the purification according to the invention, and acetic anhydride are continuously fed to the first reactor. The reaction proceeds at temperatures of from 120° to 170° C., preferably 130° to 160° C., and it is controlled in such a manner that a final conversion rate of 20 to 70, preferably 40 to 60, mol % of N,N-N',N'-tetraacetylethylenediamine, relative to N,N'-diacetylethylenediamine, is obtained. Relative to tetraacetylethylenediamine formed, a space/time yield of about 70 g/l · h is obtained.

In the case of a cascade of two reaction vessels, the reaction is carried out as follows:

N,N'-diacetylethylenediamine, the product mixture recovered after the purification according to the invention, and acetic anhydride are fed continuously and in the weight ratio as indicated to the first reactor, from where the reaction mixture having a yellow to light brown color flows into the second reactor. In the first reactor, the mixture is converted up to a rate which is lower by 25 to 50, preferably 30 to 40, % than the final conversion rate attained in the second reactor, from where the brown product mixture flows into a vessel in which it is cooled with agitation in order to stop the reaction.

In a further advantageous embodiment of the process of the invention, an amount of from 0.01 to 0.3, preferably 0.1 to 0.2, parts by weight of ketene per part by weight of N,N'-diacetylethylenediamine may be added to the reaction mixture in step (a). In the case of batchwise operation, it is added preferably after having attained the reaction temperature, and in the case of continuous operation, it is preferably introduced into the first reactor. This addition allows to reduce the reaction time and results in an increased space/time yield.

After having stopped the acetylation, the brown-colored product mixture is liberated according to the invention from the dyeing impurities.

This purification operation in accordance with the invention may be carried out by extraction, distillation or with the use of adsorbents; the two latter methods being preferred. In the purification with the use of adsorbents, commercial agents may be employed, and they are added to the reaction mixture (product mixture) either before or after separation of the tetraacetylethylenediamine, which latter compound is advantageously separated by precipitation (crystallization) due to cooling to about 0° to 30° C.

In the first case, the dark-brown reaction mixture, after having terminated (stopped) the reaction, is cooled preferably to 60°–100° C., and about 0.5 to 10, preferably about 1 to 5, weight %, relative to the weight of the reaction mixture, of a commercial bleaching earth, for example Tonsil ®AC, or active charcoal are added with agitation, and this agitation is continued at the same temperature for about 5 to 30, preferably about 5 to 10, minutes. After having removed the adsorbent by filtration, decanting or centrifugation, a light yellow solution is obtained; the treatment with adsorbents may be repeated several times, preferably 2 to 3 times. After cooling to 0° to 30° C., the colorless tetraacetyl compound is crystallized from the solution and removed by filtration, decanting or centrifugation. The filtrate having then a very light color only is reused for acetylation in the reaction process after having separated the acetic acid formed in the reaction.

In the second case, first the tetraacetylethylenediamine is separated by crystallization from the product mixture. After addition of about 0.5 to 10, preferably 1 to 5, weight %, relative to the weight of the product mixture, of bleaching earth or active charcoal to the dark-brown mother liquor having a temperature of from 20° to 110° C., preferably 60° to 100° C., further agitation for about 5 to 30, preferably 5 to 10, minutes and subsequent filtration of the adsorbent, a light yellowish solution is obtained which is reused in the reaction for the acetylation after having distilled off the acetic acid present.

A further possible purification mode consists in a distillation work-up of the mother liquor. In this case, the reaction mixture obtained is first cooled to about 0° to 30° C., and the N,N,N',N'-tetraacetylethylenediamine obtained is separated. Subsequently, excess acetic anhydride and acetic acid formed in the reaction are removed by distillation. The residue is further distilled under reduced pressure (0.4 to 8, preferably 0.5 to 1.5, mbars) at a temperature of from 140° to 240° C., preferably 150° to 200° C. As distillate there is obtained a light yellow liquid having a melting point of from 50° to 90° C., which solidifies on cooling. This distillate consisting substantially of unreacted diacetyl- and triacetylethylenediamine and a small amount of uncrystallized tetraacetylethylenediamine is recycled to the reaction together with acetic anhydride (in order to adjust the cited weight ratio). The distillation bottoms consist of a small amount of dark, tar-like product which may be rejected.

The process of the invention has several advantages. By combining (a) acetylation of diacetylethylenediamine with acetic anhydride,
(b) stop of acetylation to tetraacetylethylenediamine before complete conversion of diacetylethylenediamine used,
(c) liberation from dyeing impurities of the reaction product obtained when stopping the reaction and
(d) recycling to the acetylation of the purified reactants incompletely converted to N,N,N',N'-tetraacetylethylene diamine, a process is provided which allows the manufacture of tetraacetylethylenediamine with very high yields of more than 97%. Moreover, the tetraacetylethylenediamine obtained according to this process is nearly colorless.

A further special advantage of the process of the invention resides in the fact that, due to the complete removal of the dyeing by-products from the reaction mixture, the incompletely acetylated reaction components can be recycled quantitatively to the acetylation. Concentration of the dyeing by-products causing a dark color is thus prevented, so that the final product is practically colorless. Another advantage of the process of the invention resides in the fact that an insignificant amount only of useless and hard-to-get-rid-off by-products is formed, in contrast to hitherto known processes where up to 15 weight %, relative to diacetylethylenediamine used, of by-products are produced.

Moreover, the process of this invention can be carried out in a technologically simple manner either batchwise or continuously, and it requires a relatively short reaction time only, as compared to the known processes. Especially, the complicated operation mode of distilling off the acetic acid from the acetylation to the same extent to which it is formed is thus avoided.

The following Examples illustrate the invention.

EXAMPLE 1

72.1 g of N,N'-diacetylethylenediamine are refluxed with 306 g of acetic anhydride for 3 hours at 140° C. Subsequently, the batch is cooled to about 100° C., 9.5 g of Tonsil ®AC (bleaching earth) are added, and the whole is stirred for 10 minutes at 100° C. The batch is then filtered hot. Again 9.5 g of Tonsil ®AC are added to the filtrate, and it is stirred at 100° C. for 10 minutes again and filtered in hot state again. Due to the treatment with Tonsil ®AC, the initially dark-brown reaction mixture becomes light yellow.

The purified reaction mixture is cooled to 0° C., the precipitated colorless crystals are suction-filtered and dried at 100° C. in a vacuum drying cabinet. The yield is 72.6 g of tetraacetylethylenediamine, and the conversion rate attained when the reaction was stopped is 63.7 mol %.

In order to separate acetic acid and acetic anhydride, the mother liquor is vaporized under reduced pressure. To the oily residue of 33.1 g, 47.6 g of fresh N,N'-diacetylethylenediamine and 306 g of acetic anhydride are added. Reaction and subsequent purification of the dark-brown reaction mixture are carried out as described.

In a series of sequenced batches, the following yields of tetraacetylethylenediamine, relative to N,N'-diacetylethylenediamine used, were obtained:

TABLE 1

| Starting diacetylethylendiamine in g | Yield of tetraacetylethylenediamine in g | Yield in mol % | Stop at conversion rate in mol % |
|---|---|---|---|
| 47 | 74.2 | 98.5 | 57.6 |
| 47 | 72.6 | 96.4 | 56.7 |
| 47 | 72.0 | 95.5 | 56.8 |
| 47 | 72.7 | 96.5 | 57.3 |
| 47 | 73.3 | 97.5 | 57.8 |
| 47 | 73.8 | 97.9 | 58.2 |
| 47 | 73.1 | 97.0 | 57.7 |
| 47 | 73.3 | 97.3 | 57.8 |

The average yield of tetraacetylethylenediamine is therefore 97.0%. The average conversion rate attained on stop of the reaction is 57.0 mol %. The colorless product obtained has a melting point of 151° C. and a purity degree of 99.5%. A solution of 3 g of active substance in 100 ml of chloroform has a color number (APHA) of less than 10.

EXAMPLE 2

72.1 g of N,N'-diacetylethylenediamine are mixed with 306 g of acetic anhydride and refluxed with agitation of 3 hours at 140° C. The dark-brown mixture is then stirred for 10 minutes at 100° C. with 2% of active charcoal Brilonit ® normal, and thereafter, the active charcoal is filtered off from the hot solution. Due to the treatment with the active charcoal, the initially dark-brown solution becomes light yellow. After cooling to 15° C., the precipitated colorless crystals of tetraacetylethylenediamine are separated. The unreacted reactants contained in the mother liquor are reused in the reaction after having distilled off acetic acid and acetic anhydride.

EXAMPLE 3

72.1 g of N,N'-diacetylethylenediamine are mixed with 306 g of acetic anhydride and reacted for 3 hours at 140° C. The mixture is then cooled, and the tetraacetylethylenediamine crystallized at 0° C. is filtered off. The dark-brown mother liquor is stirred for 10 minutes at 100° C. with 15 g of Tonsil ®AC. After having filtered off the Tonsil, a light yellow solution is obtained. The unreacted reactants contained therein are reused in the reaction after having distilled off acetic acid and acetic anhydride.

EXAMPLE 4

216 g of N,N'-diacetylethylenediamine are mixed with 900 g of acetic anhydride and refluxed at 140° C. in a 2-liter flask provided with agitator and condenser. After a reaction time of 3 hours, a dark-brown reaction mixture is obtained.

This mixture is cooled to 0° C. with thorough agitation. The precipitated crystals are separated and washed with 50 ml of icecold acetic anhydride. The crystals are then dried for about 1 hour under reduced pressure and a temperature of 80° to 100° C. The yield is 226 g. The reaction is stopped at a conversion rate of 66 mol %.

Acetic acid and acetic anhydride are distilled off from the dark-brown mother liquor. 95 g of a black oily product is obtained as residue, which is subsequently distilled under a highly reduced pressure of 1 mbar. The transition temperature is 150° to 160° C. The temperature of the bottoms rises to 200° C. About 4 g of a tar-like mass remain and cannot be distilled. Relative to the yield of tetraacetylethylenediamine of 226 g, the by-products correspond to 1.8 weight % only. 91 g of a light yellow liquid are obtained as distillate, which solidifies at 50° to 90° C. This melt is refluxed again for 3 hours at 140° C. with 144 g of diacetylethylenediamine and 900 g of acetic anhydride. Subsequently, the reaction mixture is cooled to 0° C., the precipitated crystals are filtered off and washed with icecold acetic anhydride. The mother liquor is recycled to the work-up as described above. In a series of sequenced batches, the following yields of tetraacetylethylenediamine, relative to N,N'-diacetylethylenediamine, were obtained:

TABLE 2

| Starting diacetylethylenediamine in g | Yield of tetraacetylethylenediamine in g | Yield in mol % | Stop at conversion rate in mol % |
|---|---|---|---|
| 144 | 226 | 99.1 | 61 |
| 144 | 225 | 98.6 | 61 |
| 144 | 218 | 95.6 | 59 |
| 144 | 225 | 98.7 | 61 |
| 144 | 222 | 97.4 | 60 |

The average yield of tetraacetylethylenediamine is 97.9%. The colorless product obtained has a melting point of 152° C. and a purity of 99.8 %. The solution of 3 g of active substance in 100 ml of chloroform has a color number (APHA) of less than 10.

EXAMPLE 5

In a cascade of two 8-liter vessels provided with agitator and after having adjusted stationary conditions, 656 g/h of fresh N,N'-diacetylethylenediamine and 2.600 g/h of acetic anhydride are fed to the first reactor. Subsequently, 1.185 g/h of incompletely reacted reaction product consisting of N,N'-diacetylethylenediamine, the triacetylethylenediamine intermediate product and small amounts of tetraactylethylenediamine are recycled to the first reaction vessel from a purification distillation connected to the second reaction step. The temperature in both the reactors is maintained at 140° C. For crystallization, the reaction mixture is fed to a cascade consisting of two 8-liter vessels provided with agitator and cooling jacket. In the first crystallization vessel, the mixture is cooled to about 30° to 35° C. with thorough agitation. In the second crystallization vessel, the temperature is dropped to about 0° C. by means of brine cooling. The crystal pulp is separated from the mother liquor by suction-filtration, and the crystals are washed with a small amount of cold water.

After drying at 80° to 100° C. in a drying cabinet, crystals of tetraacetylethylenediamine having a purity degree of 99.5% are obtained. A solution of 3 g in 100 ml of chloroform has an APHA color number of 8. 1.015 g of tetraacetylethylenediamine are obtained per hour, which corresponds to a yield of 98%. The conversion rate at stop of the reaction is 35 mol %.

The washing water is rejected. Excess acetic anhydride and acetic acid formed in the reaction are distilled off from the mother liquor. After having removed the mixture of acetic acid/acetic anhydride from the mother liquor, an oily, dark-brown residue is obtained which solidifies at about 40° C. 1.205 g/h of this residue are obtained, which are distilled under a highly reduced pressure of 0.5 to 1.5 mbars. The product has a boiling point of 160° to 180° C. As distillate, there is obtained a light yellow liquid which solidifies at about 130° C. the amount of 1.185 g/h of distillate obtained per hour is recycled to the first reaction vessel in the manner as described.

In the distillation under highly reduced pressure, a residue of 20 g/h of tar-like substances is obtained which is rejected. It corresponds to about 2%, relative to the yield of tetraacetylethylenediamine.

What is claimed is:

1. A process for the manufacture of N,N,N',N'-tetraacetylethylenediamine by acetylation of N,N'-diacetylethylenediamine with acetic anhydride at a temperature of from 120° to 170° C., which comprises
   (a) using N,N'-diacetylethylenediamine and acetic anhydride in a weight ratio of from 1:1 to 1:10,
   (b) stopping the acetylation before the reaction equilibrium between N,N'-diacetylethylenediamine and N,N,N',N'-tetraacetylethylenediamine is attained,
   (c) purifying the brown-colored reaction mixture after or before the separation by crystallization of N,N,N',N'-tetraacetylethylenediamine, in order to remove the dyeing impurities, and
   (d) recycling the purified and recovered reaction components not completely reacted to the acetylation.

2. The process as claimed in claim 1, which comprises
   (a) using N,N'-diacetylethylenediamine and acetic anhydride in a weight ratio of from 1:1 to 1:10,
   (b) stopping the acetylation after having attained a conversion rate of from 20 to 70 mol %, relative to N,N'-diacetylethylenediamine, of N,N,N',N'-tetraacetylethylenediamine,
   (c) purifying the reaction mixture by vacuum distillation after having separated N,N,N',N'-tetraacetylethylenediamine, acetic anhydride and acetic acid, and
   (d) recycling the distillate to the acetylation.

3. The process as claimed in claim 1, which comprises
   (a) using N,N'-diacetylethylenediamine and acetic anhydride in a weight ratio of from 1:1 to 1:10,
   (b) stopping the acetylation after having attained a conversion rate of from 20 to 70 mol %, relative to N,N'-diacetylethylenediamine, of N,N,N',N'-tetraacetylethylenediamine,
   (c) purifying the reaction mixture by means of an adsorbent, and
   (d) recycling the purified and recovered reaction components not completely converted to N,N,N',N'-tetraacetylethylenediamine to the acetylation.

4. The process as claimed in claim 1, which comprises using in step (a) N,N'-diacetylethylenediamine and acetic anhydride in a weight ratio of from 1:1 to 1:5.

5. The process as claimed in 1, which comprises using in step (a) N,N'-diacetylethylenediamine and acetic anhydride in a weight ratio of from 1:1 to 1:2.5.

6. The process as claimed in claims 1 to 5, which comprises adding in step (a) from 0.01 to 0.3 parts by weight of ketene per part by weight of N,N'-diacetylethylenediamine.

7. The process as claimed in claim 3, which comprises carrying out the purification with the adsorbent by heating the product mixture to a temperature of from 60° to 100° C., adding with agitation an amount of adsorbent sufficient for adsorption of the dyeing impurities, continuing the agitation for a further 5 to 30 minutes, and subsequently filtering off the adsorbent.

8. The process as claimed in claim 7, which comprises using as adsorbent bleaching earth or active charcoal.

* * * * *